US008153102B2

(12) United States Patent
Modi et al.

(10) Patent No.: US 8,153,102 B2
(45) Date of Patent: Apr. 10, 2012

(54) **PROCESS FOR MANUFACTURING PHARMACEUTICAL COMPOSITION COMPRISES OF *MYCOBACTERIUM W* IN THE TREATMENT OF ASTHMA (OBSTRUCTIVE LUNG DISEASE)**

(75) Inventors: Rajiv Indravadan Modi, Ahmedabad (IN); Bakulesh Mafatlal Khamar, Ahmedabad (IN)

(73) Assignee: Cadila Pharmaceuticals Ltd., Ahmedabad (IN)

( * ) Notice: Subject to any disclaimer, the term of this patent is extended or adjusted under 35 U.S.C. 154(b) by 0 days.

(21) Appl. No.: 10/565,211

(22) PCT Filed: Mar. 11, 2003

(86) PCT No.: PCT/IB03/00860
§ 371 (c)(1),
(2), (4) Date: Oct. 30, 2006

(87) PCT Pub. No.: WO03/075826
PCT Pub. Date: Sep. 18, 2003

(65) Prior Publication Data
US 2007/0059328 A1     Mar. 15, 2007

(30) Foreign Application Priority Data
Mar. 13, 2002    (IN) .......................... 247/MUM/2002

(51) Int. Cl.
*A61K 49/00* (2006.01)
*A61K 39/04* (2006.01)
*A61K 39/02* (2006.01)

(52) U.S. Cl. ..... 424/9.2; 424/9.1; 424/184.1; 424/234.1; 424/248.1; 424/278.1; 424/282.1; 424/243; 424/253.1

(58) Field of Classification Search .................. 424/9.1, 424/9.2, 184.1, 234.1, 248.1, 278, 282.1, 424/278.1; 435/243, 253.1
See application file for complete search history.

(56) References Cited

FOREIGN PATENT DOCUMENTS
GB      2236480    * 10/1991

OTHER PUBLICATIONS

Hopfenspirger, M. T. et al. (2001). "*Mycobacterial* Antigens Attenuate Late Phase Response, Airway Hyperresponsiveness, and Bronchoalveolar Lavage Eosinophilia in a Mouse Model of Bronchial Asthma," *International Immunopharmacology* 1(9-10):1743-1751 Abstract, retrieved from EPOQUE Medline Database, AN: NLM11562066.

Pherwani, A. V. et al. (1992). "Bronchial Challenge with Purified Protein Derivative of *Mycobaterium tuberculosis* in Asthma," *Indian Pediatrics* 29(7):867-870, Abstract, retrieved from EPOQUE Medline Database, AN: NLM1428135.

Suzuki, N. et al. (2001). "Can *Mycobacterium tuberculosis* Infection Prevent Asthma and Other Allergic Disorders?" *International Archives of Allergy and Immunology* 124(1-3):113-116.

* cited by examiner

*Primary Examiner* — Rodney P. Swartz
(74) *Attorney, Agent, or Firm* — Burns & Levinson LLP

(57) ABSTRACT

The invention relates to process for the preparation of formulations comprising a microorganism *Mycobacterium w* for the management of bronchial Asthma (obstructive lung disease).

21 Claims, No Drawings

PROCESS FOR MANUFACTURING PHARMACEUTICAL COMPOSITION COMPRISES OF MYCOBACTERIUM W IN THE TREATMENT OF ASTHMA (OBSTRUCTIVE LUNG DISEASE)

The invention relates to process for the preparation of formulations comprising a microorganism *Mycobacterium w* for the management of bronchial Asthma (obstructive lung disease).

Obstructive lung diseases are characterized by limitation of air flow. The limitation of airflow can be due to mechanical obstruction by tumor or edema or bronchial smooth muscle contraction. Mechanical obstruction needs one time management.

Other obstructive lung diseases are progressive and/or episodic in nature.

Bronchial asthma is an ill defined group of obstructive lung diseases. It is one of the most common disorders encountered in clinical medicine in both children and adults, rather than being a single disease asthma is currently considered to be a group of different disorders (complex syndrome with many clinical phenotypes) characterized by
1. Variable degree of airflow obstruction
2. air-way inflammation
3. broncho-hyperresponsiveness.

This syndrome arises as a result of interaction between multiple genetic and environmental factors. Some patients also exhibit acute hypersensitivity responses to common inhaled proteins, known as allergens. Very small amount of them is required to trigger mast cell degranulation. However large number of patients do not have personal or family history of allergy and have negative skin tests.

Chronic inflammation is found to be underlying pathology in clinical syndrome of asthma. Histopathology of lungs reveal hyperinflation, mucous plugging in the airways, cluster of sloughed epithelial cells, and a crystalline precipitate of eosinophil derived proteins. Bronchial mucosa are edematous, the number of goblet cells is increased, the basement membrane is thickened, and the smooth muscle is hypertrophied.

Bronchial smooth muscle contraction as seen in bronchial asthma is a recurrent phenomenon. It occurs as an episodic or chronic ailment or as an episodic exacerbation of chronic disease Various definitions are given to characterize this disorder Asthma is defined as a condition wherein there is a complete or partial reversibility of obstructive dysfunction after bronchodilators therapy.

Asthma is also defined as chronic inflammatory disorder of the airways that occurs when individuals with genetic predisposition are exposed to appropriate trigger factors leading to disruption of airway epithelium, infiltration of inflammatory cells, thickening of basement membrane, as well as smooth muscle spasm and hypertrophy.

Asthma is a disease characterized by an increased responsiveness of the trachea and bronchi to various stimuli resulting in airway obstruction that is reversible, either spontaneously or as a result of treatment.

Asthma is a chronic inflammatory pulmonary disorder that is characterized by reversible obstruction of the airways.

Asthma is a chronic obstructive disease characterized by tracheo-bronchial hyper- reactivity leading to paroxysmal airway narrowing, which may reverse spontaneously or as a result of treatment. It is characterized clinically by wheezing, dyspnea, and cough. Allergic asthma is the most common form. Other precipitating factors include infection, exercise, occupational and environmental exposures, drugs, air pollution, and emotional factors.

Asthma is a chronic condition involving lungs in which narrowing of the passages from the lungs to the nose and mouth(airways) leads to difficulty breathing. These changes commonly occur in response to changes in the environment including weather, allergens (such as dog or cat dander, mold, or dust), foods, or respiratory infections (colds).

Asthma is also defined as paroxysmal or chronic dyspnea due to lung disorder.

Bronchial asthma is also defined as a disease characterized by an increased responsiveness of the trachea and bronchi to various stimuli and manifested by wide spread narrowing of the airways that changes in severity either spontaneously or as a result of treatment.

Clinically, it is characterized by:
Episodic or chronic wheezing, dyspnea, cough, and tightness in the chest.
Prolonged expiration and diffuse wheezing on physical examination.
Limitation of airflow on pulmonary function testing, or positive bronchoprovocation challenge test.
Complete or partial reversibility of obstructive dysfunction after bronchodilator therapy.

At the moment preferred first line therapy of such conditions is inhaled corticosteroids. If it is not adequate than bronchodilators like beta agonists like salmbutol, methylxanthines like theophylin anti cholinergics like ipratropium are added in form of inhaled or oral drug. Leukotriene antagonists may also be added which do not posses direct bronchodilator activity like glucocorticoids.

The management of an attack comprises the of use of bronchodilators, corticosteroids and leucotreine antagonists. They can be used orally, parenterally or in form of aerosols depending upon severity of disease and other factors. Corticosteroids and mast cell stabilizers like chromolyn sodium are also used to prevent the subsequent attack. However it is not necessary that each episode needs to be treated with bronchodilators or each patient with chronic obstructive lung disease needs to be treated by bronchodilators.

Management of severe acute attack or acute exacerbation of chronic disease may need massive dose of parenteral glucocorticoids to control the attack.

Asthma is a chronic lung disease. It cannot be cured only controlled. In asthma airways are inflamed. That is, airway linings are swollen and red. Airways narrow and breathing becomes hard. This narrowing gets better (but not all the way in some patients), sometimes by itself, some times with treatment. Airways are super sensitive. They react to many things, such as cigarette smoke, pollen, or cold air. Coughing, wheezing, tight chest, difficult breathing or an asthma episode may result following exposure to allergen.

The prevention of an attack comprises of eliminating 'trigger factors'. It includes measures to control house dust mite antigen, animal danders, avoidance of exposure to environmental factors including change place of work or residence, early treatment of upper respiratory tract and chest infections etc.

What is required in management of asthma is improvement in lung function

The present invention discloses such formulations and method of their manufacture and use.

Administration of pharmaceutical composition made as per present invention is found to result in reduction in severity of disease and frequency of asthmatic attacks. The dependence on drugs is decreased and quality of life improves.

*Mycobacterium w* is found to be useful in management of leprosy. It converts lepromin negative individuals to lepromin positive status. It also reduces the duration of therapy required for cure of multibacillary leprosy.

The pharmaceutical composition made as per present invention is found to be effective in management of asthma (obstructive lung disease)

SUMMARY OF THE INVENTION

According to the present invention, pharmaceutical composition made from '*Mycobacterium w*' (Mw)) is found to be useful in the management of asthma(obstructive lung disease).

*Mycobacterium w* used in the present invention is a non-pathogenic, cultivable, atypical mycobacterium, with biochemical properties and fast growth characteristics resembling those belonging to Runyons group IV class of Mycobacteria in its metabolic and growth properties but is not identical to those strains currently listed in this group. It is therefore thought that (Mw)) is an entirely new strain.

The species identity of Mw has been defined by polymerase chain reaction DNA sequence determination and differentiated from thirty other species of mycobacteria. It however differs from those presently listed in this group in one respect or the other. By base sequence analysis of a polymorphic region of pattern analysis, it has been established that Mw is a unique species distinct from many other known mycobacterial species examined which are: *M. avium, M. intracellulare, M. scrofulaceum, M. kansasii, M. gastri, M. gordonae, M. shimoidei, M. malmoense, M. haemophilum, M. terrae, M. nonchromogenicum, M. triviale, M. marinum, M. flavescens, M. simian, M. szulgai, M. xenopi, M. asciaticum, M. aurum, M. smegmatis, M. vaccae, M. fortuitum* subsp *fortuitum, M. fortuitum* subsp. *Peregrinum, M. chelonae* subsp. *Chelonae, M. chelonae* subsp. *Abscessus, M. genavense, M. tuberculosis, M. tuberculosis* $H_{37}R_v$, and *M. paratuberculosis*.

The object of the present invention is to provide a pharmaceutical composition containing '*Mycobacterium w*' (Mw) with or without constituents obtained from Mw for the management of asthma (obstructive lung disease). Yet another object of the present invention is to provide a pharmaceutical composition containing '*Mycobacterium w*' (Mw) with or without constituents obtained from Mw for prevention of attacks of asthma (obstructive lung disease).

Yet another object of the present invention is to provide a pharmaceutical composition containing '*Mycobacterium w*' (Mw) with or without constituents obtained from Mw for delaying attacks of bronchial asthma (obstructive lung disease).

Yet another object of the present invention is to provide a pharmaceutical composition containing '*Mycobacterium w*' (Mw) with or without constituents obtained from Mw which reduces the requirement of drugs used to improve lung function in management of asthma(obstructive lung disease).

Yet another object of the present invention is to provide a pharmaceutical composition containing '*Mycobacterium w*' (Mw) with or without constituents obtained from Mw which improves lung function in presence/absence of other drugs in asthma (obstructive lung disease).

DETAILED DESCRIPTION OF THE INVENTION

In accordance with the invention the composition containing *Mycobacterium w* , the method of preparation, HPLC characteristic, its safety and tolerability, methods of use and outcome of treatments are described in following examples. The following are illustrative examples of the present invention and scope of the present invention should not be limited by them.

EXAMPLE 1

The Pharmaceutical Compositions

A. Each dose of 0.1 ml of therapeutic agent contains:

| | |
|---|---|
| *Mycobacterium* w., (heat killed) | $0.50 \times 10^9$ |
| Sodium Chloride I.P. | 0.90% w/v |
| Tween 80 | 0.1% w/v |
| Thiomerosal I.P. | 0.01% w/v |
| (As a Preservative) | |
| Water for injection I.P. | q.s. to 0.1 ml |

B. Each dose of 0.1 ml of therapeutic agent contains:

| | |
|---|---|
| *Mycobacterium* w., (heat killed) | $0.50 \times 10^9$ |
| Sodium Chloride I.P. | 0.90% w/v |
| Triton x 100 | 0.1% w/v |
| Thiomerosal I.P. | 0.01% w/v |
| (As a Preservative) | |
| Water for injection I.P. | q.s. to 0.1 ml |

C. Each dose of 0.1 ml of therapeutic agent contains:

| | |
|---|---|
| *Mycobacterium* w., (heat killed) | $0.50 \times 10^9$ |
| Sodium Chloride I.P. | 0.90% w/v |
| Thiomerosal I.P. | 0.01% w/v |
| (As a Preservative) | |
| Water for injection I.P. | q.s. to 0.1 ml |

D. Each dose of 0.1 ml of therapeutic agent contains

| | |
|---|---|
| Extract of *Mycobacterium* w after sonication from $1 \times 10^{10}$ *Mycobacterium* w | |
| Sodium Chloride I.P. | 0.90% w/v |
| Thiomerosal I.P. | 0.01% w/v |
| (As a Preservative) | |
| Water for injection I.P. | q.s. to 0.1 ml |

E. Each dose of 0.1 ml of therapeutic agent contains

| | |
|---|---|
| Methanol Extract of $1 \times 10^{10}$ *Mycobacterium* w | |
| Sodium Chloride I.P. | 0.90% w/v |
| Thiomerosal I.P. | 0.01% w/v |
| (As a Preservative) | |
| Water for injection I.P. | q.s. to 0.1 ml |

F. Each dose of 0.1 ml of therapeutic agent contains

| | |
|---|---|
| Chloroform Extract of $1 \times 10^{10}$ *Mycobacterium* w | |
| Sodium Chloride I.P. | 0.90% w/v |
| Thiomerosal I.P. | 0.01% w/v |

-continued

| Chloroform Extract of $1 \times 10^{10}$ Mycobacterium w | |
|---|---|
| (As a Preservative) | |
| Water for injection I.P. | q.s. to 0.1 ml |

G. Each dose of 0.1 ml of therapeutic agent contains

| Acetone Extract of $1 \times 10^{10}$ Mycobacterium w | |
|---|---|
| Sodium Chloride I.P. | 0.90% w/v |
| Thiomerosal I.P. | 0.01% w/v |
| (As a Preservative) | |
| Water for injection I.P. | q.s. to 0.1 ml |

H. Each dose of 0.1 ml of therapeutic agent contains

| Ethanol Extract of $1 \times 10^{10}$ Mycobacterium w | |
|---|---|
| Sodium Chloride I.P. | 0.90% w/v |
| Thiomerosal I.P. | 0.01% w/v |
| (As a Preservative) | |
| Water for injection I.P. | q.s.to 0.1 ml |

I. Each dose of 0.1 ml of therapeutic agent contains

| Liticase Extract of $1 \times 10^{10}$ Mycobacterium w | |
|---|---|
| Sodium Chloride I.P. | 0.90% w/v |
| Thiomerosal I.P. | 0.01% w/v |
| (As a Preservative) | |
| Water for injection I.P. | q.s. to 0.1 ml |

J. Each dose of 0.1 ml of therapeutic agent contains

| Mycobacterium w (heat killed) $0.5 \times 10^7$ Extract of mycobacterium w obtained $1 \times 10^3$ Mycobacterium w by disruption, solvent extraction or enzymatic extraction. | |
|---|---|
| Sodium Chloride I.P. | 0.90% w/v |
| Thiomerosal I.P. | 0.01% w/v |
| (As a Preservative) | |
| Water for injection I.P. | q.s. to 0.1 ml |

EXAMPLE 2

The Process of Preparing a Pharmaceutical Composition

A. Culturing of Mycobacterium w.
i) Preparation of culture medium.
Mycobacterium w is cultured on solid medium like L J medium or liquid medium like Middlebrook medium or sauton's liquid medium.
For better yield Middlebrook medium is enriched. It can be preferably enriched by addition of glucose, bactotryptone, and BSA. They are used in ratio of 20:30:2 preferably.
The enrichment medium is added to Middlebrook medium. It is done preferably in ratio of 15:1 to 25:1 more preferably in ratio of 20:1.
ii) Bioreactor operation
a) Preparation of vessel:
p The inner contact parts of the vessel (Joints, mechanical seals, o-ring/gasket grooves, etc.) should be properly cleaned to avoid any contamination. Fill up the vessel with 0.1 N NaOH and leave as such for 24 H to remove pyrogenic materials and other contaminants. The vessel is then cleaned first with acidified water, then with ordinary water. Finally, the vessel is rinsed with distilled water (3 times) before preparing medium.
b) Sterilization of bioreactor
The bioreactor containing 9L distilled water is sterilized with live steam(indirect). Similarly the bioreactor is sterilized once more with Middlebrook medium. The other addition bottles, inlet/outlet air filters etc. are autoclaved (twice) at 121° C. for 15 minutes. Before use, these are dried at 50° C. oven.
c) Environmental parameter
  i. Temprature: 37±0.5° C.
  ii. pH : 6.7 to 6.8 initially.
B. Harvesting and concentrating
It is typically done at the end of $6^{th}$ day after culturing under aseptic condition. The concentration of cells (pelletization) is done by centrifugation.
C. Washing of cells
The pellet so obtained is washed minimum three times with normal saline. It can be washed with any other fluid which is preferably isotonic.
D. Adding pharmaceutically acceptable carrier.
Pyrogen free normal saline is added to pellet. Any other pyrogen free isotonic fluid can be used as a pharmaceutical carrier. The carrier is added in amount so as get to desired concentration of active in final form.
E. Adding preservative
To keep the product free from other contaminating bacteria for its self life preservative is added. Preferred preservative is thiomerasol which is used in final concentration of 0.01% w/v.
F. Terminal Sterilization
Terminal sterilization can done by various physical methods like application of heat or ionizing radiation or sterile filtration.
Heat can be in the form of dry heat or moist heat. It can also be in the form of boiling or pasteurization.
Ionizing radiation can be ultraviolet or gamma rays or mircrowave or any other form of ionizing radiation.
It is preferable to autoclave the final product.
This can be done before and after filling in a final packaging.
G. Quality Control
  i. The material is evaluated for purity, sterility.
  ii. The organisms are checked for acid fastness after gram staining.
  iii. Inactivation test : This is done by culturing the product on L J medium to find out any living organism.
  iv. Pathogenicity and/or contamination with pathogen.
  The cultured organisms are administered into Balb/c mice. None of the mice should die and all should remain healthy and gain weight. There should not be any macroscopic or microscopic lesions seen in liver, lung spleen or any other organs when animals are killed up to 8 weeks following treatment.
  v. Biochemical Test:
  The organism is subjected to following biochemical tests:
  a) Urease
  b) Tween 80 hydrolysis
  c) Niacin test d) Nitrate reduction test The organism gives negative results in urease, tween 80 hydrolysis and niacin test. It is positive by nitrate reduction test.

H. Preparation of constituents of *Mycobacterium w*.

The constituents of *Mycobacterium w* can be prepared for the purpose of invention by:

I. Cell disruption
II. Solvent extraction
III. Enzymatic extraction.

The cell disruption can be done by way of sonication or use of high pressure fractionometer or by application of osmotic pressure ingredient.

The solvent extraction can be done by any organic solvent like chloroform, ethanol, methanol, acetone, phenol, isopropyl alcohol, acetic acid, urea, hexane etc.

The enzymatic extraction can be done by enzymes which can digest cell wall/membranes. They are typically proteolytic in nature. Enzyme lyticase and pronase are the preferred enzymes. For the purpose of invention cell constituents of *Mycobacterium w* can be used alone in place of *Mycobacterium w* organisms or it can be added to the product containing *Mycobacterium w*.

Addition of cell constituents results in improved efficacy of the product.

EXAMPLE 3

Characteristics of Constituents of *Mycobacterium w* by HPLC Analysis.

The constituents of *Mycobacterium w*. used for the purpose of invention when subjected to HPLC analysis gives a single peak at 11 minutes. No other significant peaks are found beyond. The peak is homogenous and devoid of any notch suggesting homogeneity of material obtained HPLC analysis was done using a waters system high performance liquid chromatography apparatus Column: Novapak c1860A, 4 μm, 3.9×150 mm.
The guard column: Novapak c 18
Column Temperature: 30° C.
Flow rate: 2.5 ml/min
Injection volume: 25 μL.
Mobile phase:
Solvent A: HPLC grade methanol.
Solvent B: HPLC grade methylene chloride
Binary gradient:
The HPLC gradient initially comprised 98%(v/v) methanol (solvent B).
The gradient was increased linearly to 80%.
A and 20% B at one minute; 35% A and 65% B at 10 minutes, held for 5 seconds and then decreased over 10 seconds back to 98% A and 2% B.

EXAMPLE 4

The Effect of Pharmaceutical Compositions and Methods of Use

A symptomatic patient with severe form of asthma. Her breathlessness was not controlled even though she was on a maximal medical therapy for asthma was given *Mycobacterium w* containing pharmaceutical composition (as provided in Example 1A of this invention). By four weeks patient became asymptomatic and number of drugs were gradually discontinued. Patient remained asymptomatic in spite of that.

Thus *Mycobacterium w* is found to be useful in management of asthma in making patient asymptomatic when maximal medical therapy fails to achieve this.

It is also useful in reducing the number of medicines a patient is taking.

EXAMPLE 5

The Effect of Pharmaceutical Compositions and Methods of Use

A group of patients who were getting exacerbation of disease periodically were given *Mycobacterium w* containing pharmaceutical composition (as provided in Example 1A of this invention). It was observed that none of them had exacerbation of disease.

Thus *Mycobacterium w* is found to be useful in eliminating/delaying exacerbation of the disease.

EXAMPLE 6

The Effect of Pharmaceutical Compositions and Methods of Use

Several patients diagnosed to have bronchial asthma were given conventional therapy in the form of bronchodilators and steroids. This resulted in improvement in lung function as determined by spirometry in terms of $FEV_1$ and PEFR. The improvement with therapy was in the range of 15 to 20% from baseline, over a three month period of observation and it did not improve further. At the end of three months patients were administered *Mycobacterium w* containing pharmaceutical compositions (as provided in Example 1A of this invention). It was administered as a dosage of 0.1 ml; the dosage was administered at the interval of one per week. Though these compositions are not known to have anti-inflammatory or broncho-dilator activity their administration resulted in further improvement in lung function as determined by $FEV_1$ and PEFR values. This improvement was in the range of 15 to 20% over and above the maximum values already achieved by conventional therapy.

The improvement in lung function was associated with subjective feeling of well being and improvement in quality of life. It also improved their performance scale. It also resulted in improvement in amount of physical exertion they can do without getting breathless.

Thus *Mycobacterium w* is useful in improving lung function, quality of life and performance.

EXAMPLE 7

The Effect of Pharmaceutical Compositions and Methods of Use

In a group of patients having obstructive lung disease (chronic obstructive pulmonary disease, chronic bronchitis) and who were controlled by conventional therapy were observed for a period of three months and then *Mycobacterium w* containing compositions (as provided in Example 1A) were added to the therapy and observed for another three months. Average requirement of antibiotics used to treat infections and associated exacebation of disease in the initial three months was 3.71. In the next three months when *Mycobacterium w* was coadministered the requirement came down to 2 from 3.71. None of them needed any antibiotic in last month of combined therapy.

Thus *Mycobacterium w* is useful in reducing requirement of antibiotics.

EXAMPLE 8

The Effect of Pharmaceutical Compositions and Methods of Use

In a group of patients having obstructive lung disease (bronchial asthma, chronic bronchitis) and who were controlled by conventional therapy but still requiring hospitalization from time to time for management of acute exacerbations were observed for a period of three months and *Mycobacterium w* containing compositions (as provided in Example 1A of this invention) were added to the therapy and observed for another three months. The dosage was administered intradermally every fortnight for three months. The number of exacerbations were found to be three per person in first part of the study. In the second part it came down to one per person.

Thus *Mycobacterium w* is useful in reducing the number of exacerbation of disease.

We claim:

1. A method of treating or managing obstructive lung disease comprising administering to a patient a pharmaceutical composition comprising an effective amount of a medicament selected from the group consisting of:
   (a) heat killed whole cell *Mycobacterium w*,
   (b) sonicated *Mycobacterium w*,
   (c) a solvent extract of *Mycobacterium w*, wherein the solvent is selected from the group consisting of chloroform, ethanol, methanol, and acetone,
   (d) an enzymatic extraction of *bacterium w*, wherein the enzyme is liticase, and
   (e) admixtures thereof.

2. A method of treating or managing obstructive lung disease comprising administering to a patient a pharmaceutical composition comprising an effective amount of heat killed whole cell *Mycobacterium w*.

3. The method of claim 1 or 2, wherein the method is for treating or managing asthma.

4. The method of claim 3, wherein the method is for delaying attacks of asthma.

5. The method of claim 3, wherein the method is for reducing the requirement of drugs used to improve lung function during the management of asthma.

6. The method of claim 3, wherein the method is for improving lung function in the presence or absence of other drugs.

7. The method of claim 3, wherein the asthma is bronchial asthma.

8. The method of claim 2, wherein the pharmaceutical composition comprises an admixture of heat killed whole cell *Mycobacterium w* and sonicated *Mycobacterium w*.

9. The method of claim 1, wherein the pharmaceutical composition comprises sonicated *Mycobacterium w*.

10. The method of claim 1, wherein the pharmaceutical composition comprises a solvent extract of *Mycobacterium w* wherein the solvent is selected from the group consisting of chloroform, ethanol, methanol and acetone.

11. The method of claim 1 or 2, wherein the pharmaceutical composition further comprises an adjuvant.

12. The method of claim 11, wherein the adjuvant is selected from the group consisting of mineral oil, mineral oil and surfactant, Ribi adjuvant, Titer-max, syntax adjuvant formulation, aluminum salt adjuvant, nitrocellulose adsorbed antigen, immune stimulating complexes, Gebru adjuvant, super carrier, elvax 40w, L-tyrosine, monatanide (manideoleate compound), Adju prime, Squalene, Sodium phthalyl lipopoly saccharide, calcium phosphate, saponin, melonoma antigen and muramyl dipeptide (MDP).

13. The method of claim 1 or 2, wherein the pharmaceutical composition further comprises a surfactant.

14. The method of claim 13, wherein the surfactant is polyoxyethylene sorbitan monooleate (Tween 80) or Titon X100.

15. The method of claim 13, wherein the surfactant is present in the pharmaceutical composition in a concentration of up to 0.4%.

16. The method of claim 13, wherein the surfactant is present in the pharmaceutical composition in a concentration of up to 0.1%.

17. The method of claim 1 or 2, wherein the pharmaceutical composition further comprises a preservative.

18. The method of claim 17, wherein the preservative is Thiomerosal and is present in a concentration of 0.01% w/v.

19. The method of claim 1, wherein the pharmaceutical composition is in a unit dosage form comprising at least $10^5$ *Mycobacterium w* as:
   (a) $10^5$ heat killed whole cell *Mycobacterium w*
   (b) $10^5$ sonicated *Mycobacterium w*,
   (c) a solvent extract of $10^5$ *Mycobacterium w* wherein the solvent is selected from chloroform, ethanol, methanol and acetone, or
   (d) an enzymatic extraction of $10^5$ *Mycobacterium w* wherein the enzyme is liticase.

20. The method of claim 1, wherein the pharmaceutical composition is in a unit dosage form comprising at least $10^7$ *Mycobacterium w* as:
   (a) $10^7$ heat killed whole cell *Mycobacterium w*,
   (b) $10^7$ sonicated *Mycobacterium w*,
   (c) a solvent extract of $10^7$ *Mycobacterium w*, wherein the solvent is selected from the group consisting of chloroform, ethanol, methanol, and acetone, or
   (d) an enzymatic extraction of $10^7$ *Mycobacterium w* wherein the enzyme is liticase.

21. The method of claim 1, wherein the pharmaceutical composition is in a unit dosage form comprising between $10^8$ and $10^9$ *Mycobacterium w* as:
   (a) between $10^8$ and $10^9$ heat killed whole *Mycobacterium w*,
   (b) between $10^8$ and $10^9$ sonicated Mycobacterium w,
   (c) a solvent extract of between $10^8$ and $10^9$ *Mycobacterium w* wherein the solvent is selected from the group consisting of chloroform, ethanol, methanol and, acetone, or
   (d) an enzymatic extraction of between $10^8$ and $10^9$ *Mycobacterium w* wherein the enzyme is liticase.

* * * * *